US012746196B2

(12) United States Patent
Dodd

(10) Patent No.: US 12,746,196 B2
(45) Date of Patent: Sep. 29, 2026

(54) METHOD OF MANUFACTURING A DETANGLER CONDITIONER FOR HAIR

(71) Applicant: Dawna M. Dodd, Baltimore, MD (US)

(72) Inventor: Dawna M. Dodd, Baltimore, MD (US)

( * ) Notice: Subject to any disclaimer, the term of this patent is extended or adjusted under 35 U.S.C. 154(b) by 0 days.

(21) Appl. No.: 19/161,655

(22) PCT Filed: Mar. 4, 2024

(86) PCT No.: PCT/US2024/018392

§ 371 (c)(1),
(2) Date: Sep. 2, 2025

(87) PCT Pub. No.: WO2024/182804

PCT Pub. Date: Sep. 6, 2024

(65) Prior Publication Data

US 2026/0130843 A1 May 14, 2026

(30) Foreign Application Priority Data

Mar. 2, 2023 (AU) ................................ 2023900541

(51) Int. Cl.

| | |
|---|---|
| ***A61K 8/9794*** | (2017.01) |
| ***A61K 8/04*** | (2006.01) |
| ***A61K 8/23*** | (2006.01) |
| ***A61K 8/92*** | (2006.01) |
| ***A61K 8/9789*** | (2017.01) |
| ***A61Q 5/06*** | (2006.01) |
| ***A61Q 5/12*** | (2006.01) |

(52) U.S. Cl.

CPC ............ *A61K 8/9794* (2017.08); *A61K 8/044* (2013.01); *A61K 8/23* (2013.01); *A61K 8/922* (2013.01); *A61K 8/9789* (2017.08); *A61Q 5/06* (2013.01); *A61Q 5/12* (2013.01); *A61K 2800/5922* (2013.01); *A61K 2800/85* (2013.01)

(58) Field of Classification Search

None

See application file for complete search history.

(56) References Cited

U.S. PATENT DOCUMENTS

| | | | |
|---|---|---|---|
| 10,639,253 | B2 | 5/2020 | Pesaro et al. |
| 2005/0129643 | A1 | 6/2005 | Lepilleur et al. |
| 2010/0322887 | A1 | 12/2010 | Aoki et al. |
| 2014/0302103 | A1 | 10/2014 | Carter et al. |

FOREIGN PATENT DOCUMENTS

WO 2022245788 A1 11/2022

*Primary Examiner* — Nicole P Babson

(57) ABSTRACT

A method of manufacturing a detangler solution that may be easily prepared, and that helps disentangle, condition, and restore hair to a healthier state is provided. The method includes usage of all natural, plant based, biodegradable, inexpensive, quick, and easy to produce ingredients and involves easy preparation methods. To that end, the detangler solution is made from natural ingredients such as potatoes, onion, rice, fenugreek, and sulfur. More specifically, a combination of potato water, fermented onion water, and fermented rice water, form the base of the detangler solution. Further, ingredients like rosemary, dandelion root, and neem leaves are added for additional benefits. Furthermore, the detangler solutions includes an essential oil of choice for added fragrance. The detangler solution may be left in or washed out with no side effects.

18 Claims, 7 Drawing Sheets

METHOD OF MANUFACTURING A DETANGLER CONDITIONER FOR HAIR

FIELD OF THE INVENTION

The present invention generally relates to a system and method of manufacturing a detangler. More specifically, the present invention is a method of making a mixture that can disentangle and restore hair to a healthy state.

BACKGROUND OF THE INVENTION

A detangler spray is used as a leave-in conditioner that not only makes the combing process a lot easier but can also improve overall hair health. Some detanglers feature hair shinning ingredients, while others help with the protection. While many hair disentangling shampoos, conditioners, and devices exist, a detangler that can work as a conditioner, is organic, and can be made easily with natural and cost-efficient ingredients is a rare find in the current market. Further, most of the detanglers available in the market are not recommended to be used on eyelashes and eyebrows.

An objective of the present invention is to provide users with a hair detangler that can also give the appearance of fullness for the eyelashes and eyebrows. Further, the detangler solution manufactured according to the method described in the present invention is all natural, plant based, biodegradable, inexpensive, quick and easy to produce and assemble. Users are able to comb through tangled dry and wet hair immediately and thinning and balding hair has the appearance of fullness. Further, users are going to get fuller looking, stronger, healthier, conditioned strands of hair after using the detangler of the present invention. Furthermore, the detangler rids the hair of oils and dandruff and is great for eyebrows and elongates eyelashes if there are hair follicles still present. After application, one is able to comb through hair immediately. Additionally, the detangler of the present invention cleans the cell walls on the scalp and allows them to be flexible and permeable. The present invention may be left in or washed out with no side effects.

SUMMARY

The present invention is a method of manufacturing a detangler solution that may be easily prepared, and that helps disentangle, condition, and restore hair to a healthier state. To that end, the method comprises usage of all natural, plant based, biodegradable, inexpensive, quick, and easy to produce ingredients and involves easy preparation methods. More specifically, the present invention is a detangler solution made from natural ingredients such as potatoes, onion, rice, fenugreek, and sulfur. The detangler may be used to provide the appearance of fullness for the eyelashes and eyebrows. Users are able to comb through tangled dry and wet hair immediately and thinning and balding hair has the appearance of fullness. Further, users are going to get fuller looking, stronger, healthier, conditioned strands of hair after using the detangler of the present invention. Furthermore, the present invention rids the hair of oils and dandruff and is great for eyebrows and elongates eyelashes if there are hair follicles still present. After application, a user is able to comb through hair immediately. Additionally, the detangler according to the present invention cleans the cell walls of the scalp and allows them to be flexible and permeable. The present invention may be left in or washed out with no side effects.

DETAIL DESCRIPTIONS OF THE INVENTION

Figure 1:
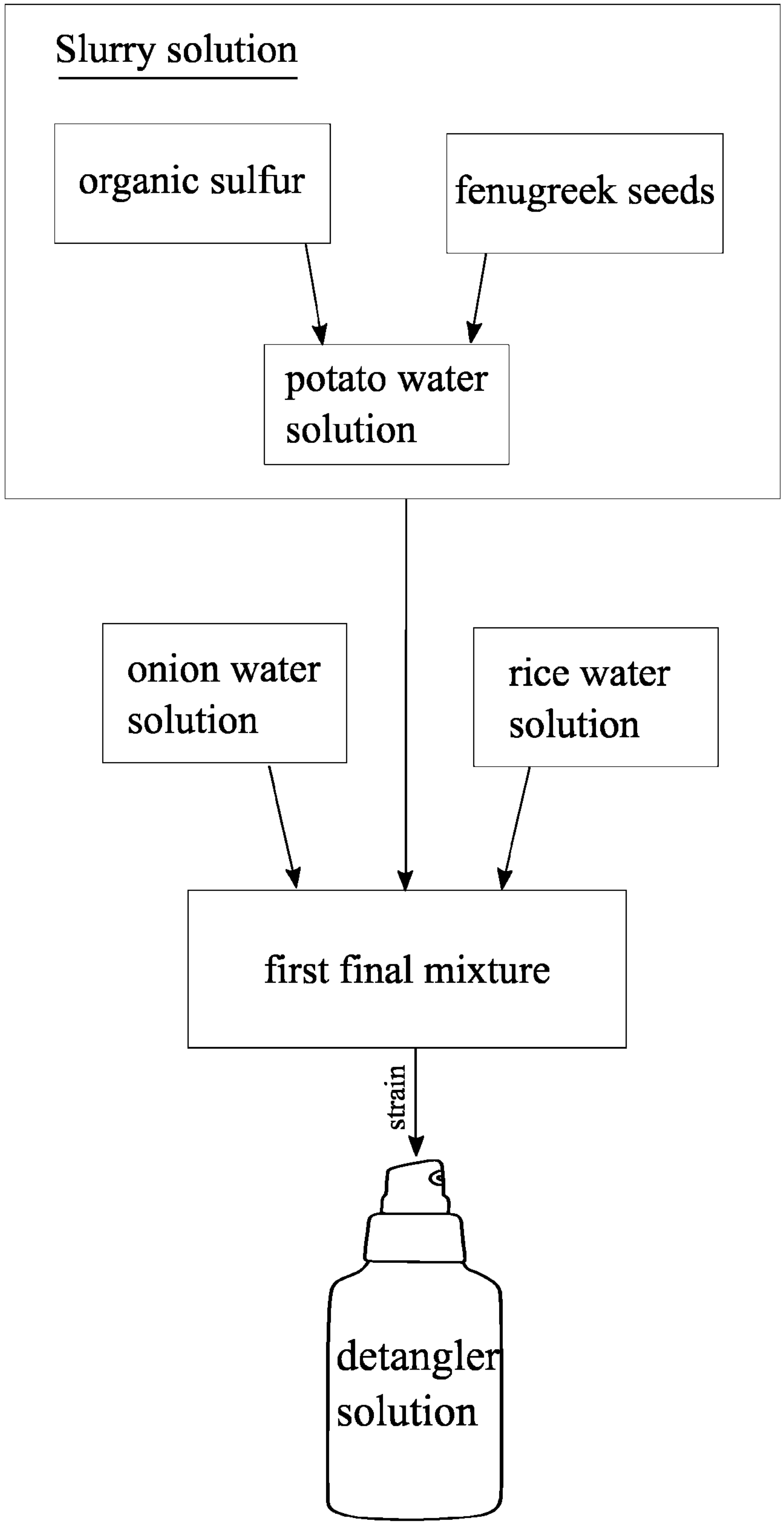
FIG. 1 is a schematic view of preparing a detangler solution according to a preferred embodiment of the present invention.
Figure 2:
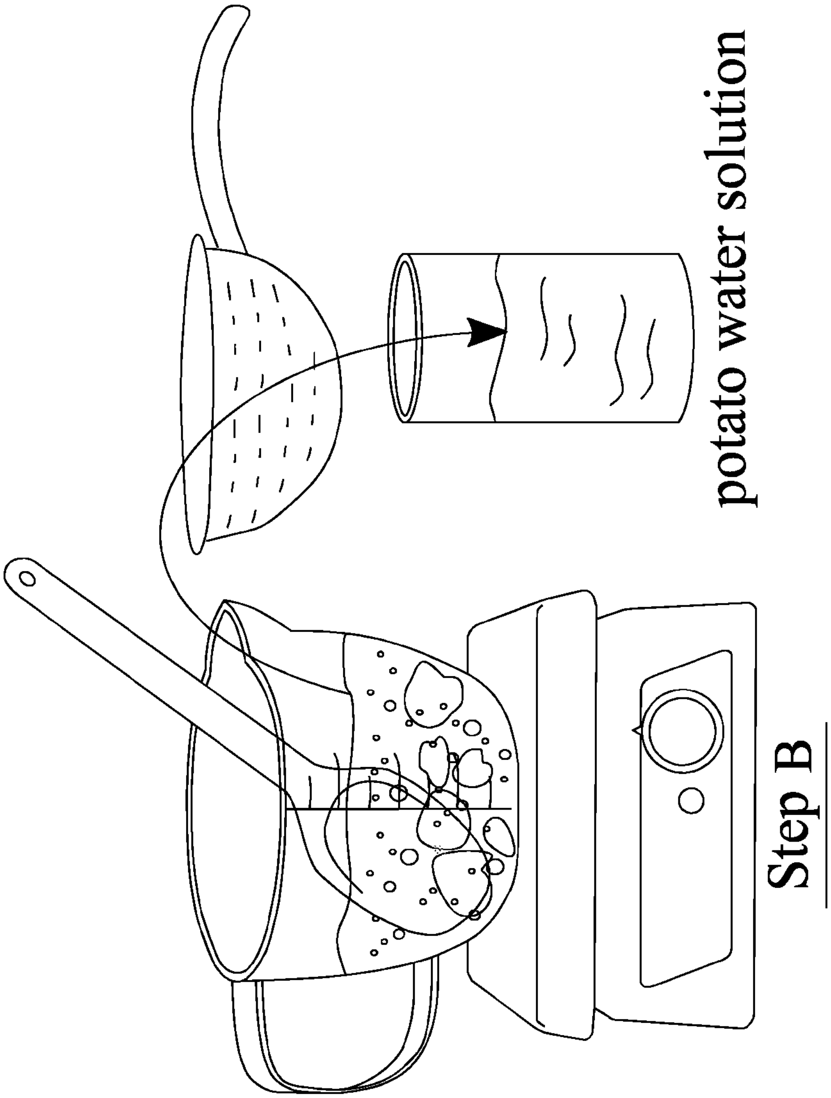
FIG. 2 is a schematic view of preparing a potato water solution.
Figure 3:
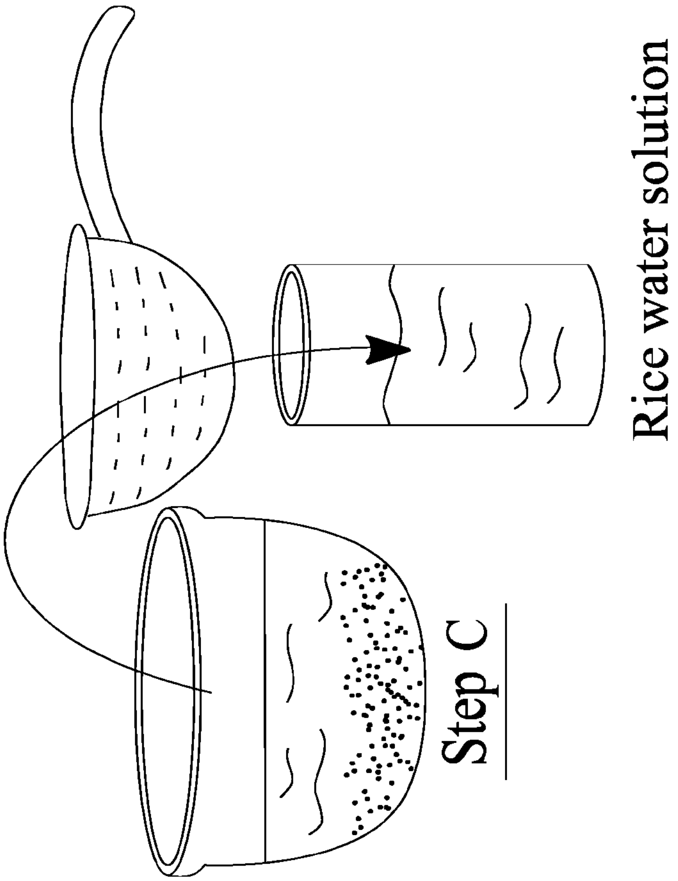
FIG. 3 is a schematic view of preparing a rice water solution.
Figure 4:
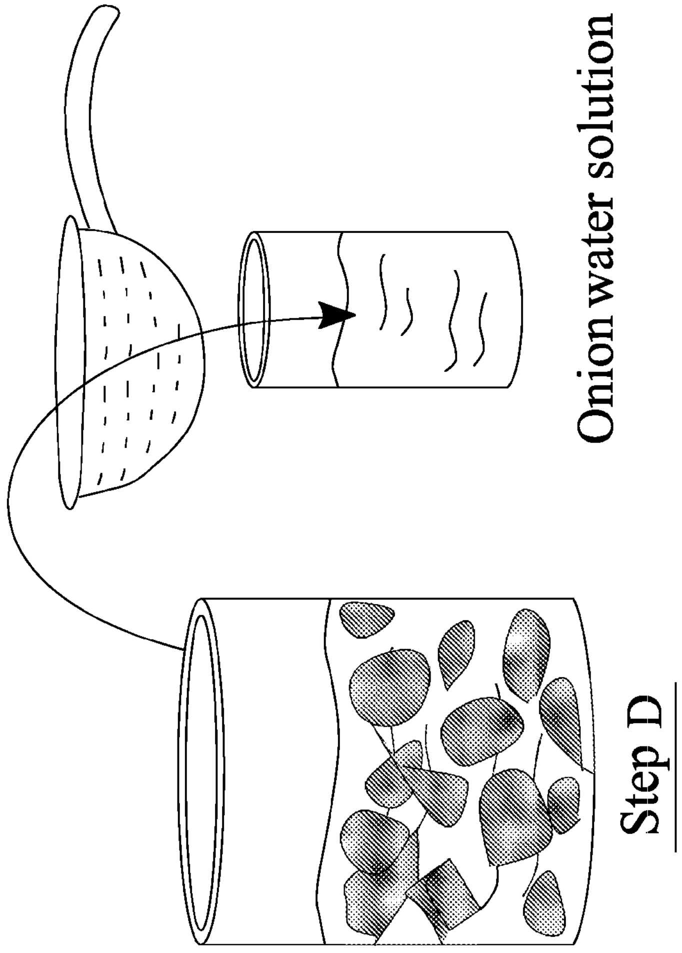
FIG. 4 is a schematic view of preparing an onion water solution.
Figure 5:
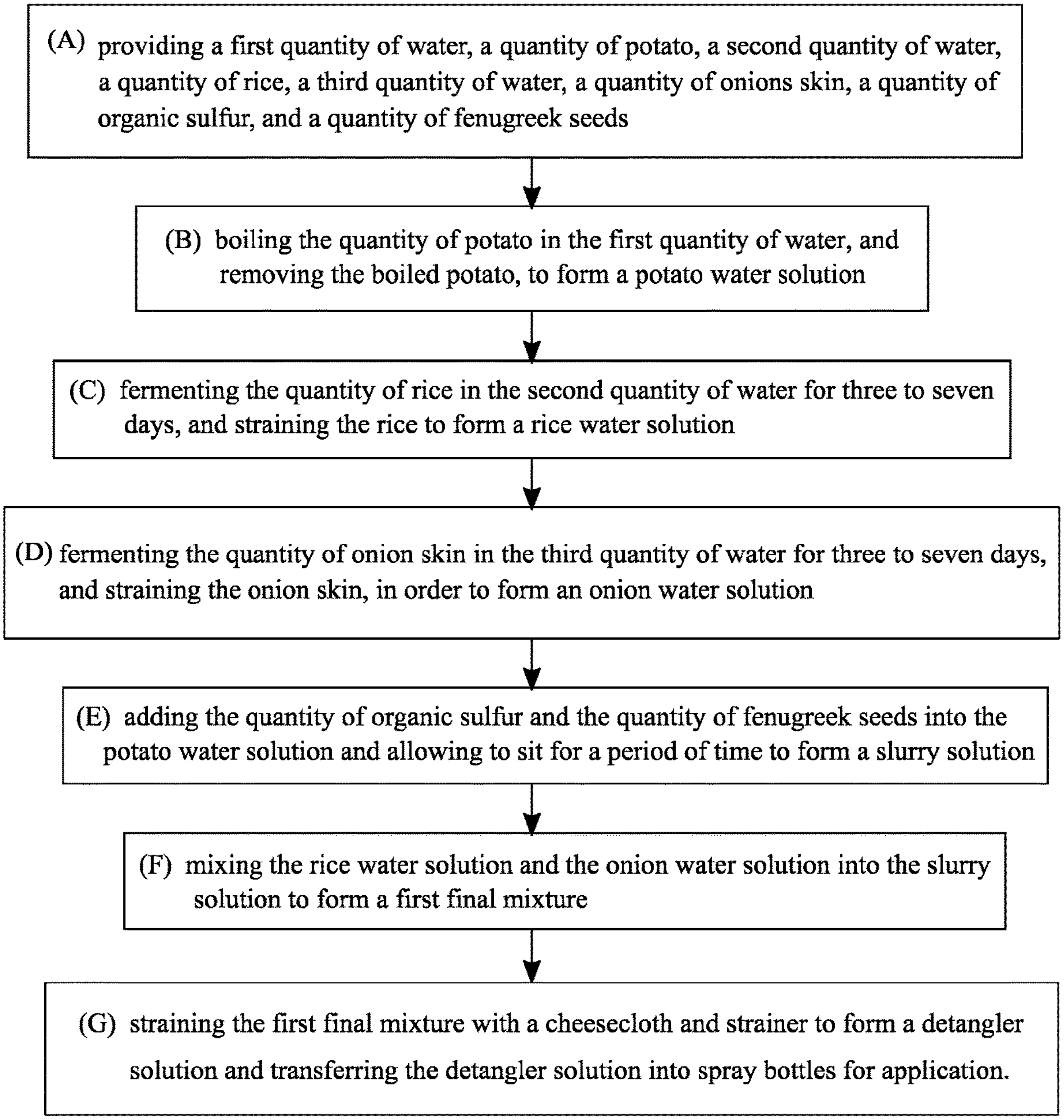
FIG. 5 is a flowchart illustrating an overall process for a method of the present invention.

All illustrations of the drawings are for the purpose of describing selected versions of the present invention and are not intended to limit the scope of the present invention.

The present invention is a system and method of manufacturing a detangler or conditioner for hair.

The following description is in reference to FIG. 1 through FIG. 7. According to a preferred embodiment, the system for manufacturing the present invention are the ingredients. To that end, an overall process or a method of manufacturing the hair detangler according to the present invention comprises, providing a first quantity of water, a quantity of potato, a second quantity of water, a quantity of rice, a third quantity of water, a quantity of onions skin, a quantity of organic sulfur, and a quantity of fenugreek seeds (Step A). In other words, the above ingredients constitute the system of the present invention. Primarily, the recipe for making the present invention comprises three types of waters, that are made from potato, onion, and rice. To that end, the method of manufacturing the detangler mixture comprises boiling the quantity of potato in the first quantity of water, and removing the boiled potato, to form a potato water solution (Step B). Preferably, the quantity of potatoes is approximately five pounds, and the first quantity of water is approximately four gallons of filtered acidic water with a PH (potential of hydrogen) level that is below nine. Potatoes make the water starchy and also add protein to the potato water solution. The PH level is preferred to be 7 because PH-7 filtered water is acidic in nature and they help fight germs. In other words, the potato water may be made by adding 5 pounds of potatoes in 4 gallons of filtered water that is at a preferable PH 7 level. To accommodate the quantity of potatoes and the first quantity of water, a pot that has at least 4-gallon capacity is chosen. Further, the potatoes are boiled until done and removed, wherein the remaining water constitutes the potato water solution.

The overall process continues by fermenting the quantity of rice in the second quantity of water for three to seven days, and straining the rice, to form a rice water solution (Step C). Soaking is the safest method to extract minerals from rice, and boiling is also another easy method. However, the fermented rice water is more potent and is richer in minerals, antioxidants and vitamin E than rice water created through other methods. Further, fermented rice water has the right PH levels for the detangler solution. Preferably, the second quantity of water is approximately 24 ounces of filtered acidic water with a PH (potential of hydrogen) level that is below 9, and the quantity of rice is approximately half a cup. Thus, in order to make the rice water solution, half cup of white rice is added to 24 ounces of filtered acidic water, that is at a preferred PH level of 7. Furthermore, the rice is allowed to soak and ferment for three to seven days, and the rice is strained from that liquid to form a rice water solution.

The overall process further continues by fermenting the quantity of onion skin in the third quantity of water for three to seven days, and straining the onion skin, in order to form an onion water solution (Step D). Onion is rich in sulfur and is known to minimize breakage and treat thinning hair. Onions have both antibacterial properties that help fight infections of the scalp and boost hair growth. It is also a known fact that red onion can give nourishing, dandruff-free hair. In other words, red onion is a storehouse of sulfur and is rich in anti-bacterial and anti-fungal properties. It has been used to strengthen hair and give all the nutrients hair needs for healthy hair growth. Not just onion but onion peels are rich in antioxidants and may be used for promoting healthy and stronger hair. Preferably, the third quantity of water is approximately 24 ounces of filtered acidic water with a PH level that is below 9, and the quantity of onion skin is approximately 24 ounces. Thus, in order to make the onion water solution, 24 ounces of red onion peel or skin is added to 24 ounces of filtered acidic water, that is at a preferred PH level of 7. Further, the onion peel is allowed to soak and ferment for three to seven days, and then strained afterwards from the liquid to form the onion water solution.

The overall process further continues by adding the quantity of organic sulfur and the quantity of fenugreek seeds into the potato water solution and allowing to sit for a period of time to form a slurry solution (Step E). Sulfur cleans the cell walls of the scalp and allows the solution to be more permeable. Sulfur also stimulates growth. Fenugreek seeds are a rich source of iron and protein, that are two essential nutrients for hair growth. They also contain a unique composition of plant compounds, including flavonoids and saponins. These compounds are presumed to induce hair growth due to their anti-inflammatory and anti-fungal effects. Further, they control scalp inflammation and pain in hair roots. Also, fenugreek contains natural antioxidants that help in fighting off the oxidative stress caused by free radicals in hair follicle cells. Fenugreek contains mucilaginous fiber that absorbs moisture tremendously. Thus, fenugreek helps in maintaining the moisture barrier in hair strands, improving the shine, and imparting softer texture. The rich content of iron and potassium present in fenugreek helps users deal with premature greying problems efficiently. Furthermore, fenugreek balances the deficit of minerals required for sufficient melanin production in hair follicles, which gives the dark color to hair naturally. Additionally, fenugreek provides increased softness and luster to hair. Preferably, each of the quantity of fenugreek seeds and the quantity of organic sulfur is two tablespoons. More specifically, after cooking the potatoes and removing the potatoes from the hot potato water, 2 tablespoons of organic sulfur and 2 tablespoons of fenugreek seeds are added into the potato water solution, and they are let to seep and cool down, or sit for about a half an hour.

The overall process comprises the step of mixing the rice water solution and the onion water solution into the slurry solution to form a first final mixture (Step F). Preferably, (Step F) is performed only after the slurry solution has cooled down to room temperature. The onion water solution and the rice water solution are added into the pot containing the slurry solution. Subsequently, the overall process continues by straining the first final mixture with a cheesecloth and strainer to form a detangler solution and transferring the detangler solution into spray bottles for application. It should be noted that the quantities of potato water, onion water, rice water, fenugreek, and sulfur may be proportionately varied, and introduced in different forms, as long as the intents of the present invention are not altered. Further, any other kinds of equipment, such as pots, strainers, storage containers, etc., and application methods that are known to one of ordinary skill in the art may be used for preparing and applying the detangler solution, as long as the objectives of the present invention are fulfilled.

In a first alternate embodiment of the present invention, the detangler solution is made through a method comprising the steps of boiling the quantity of potatoes, the quantity of rice, the quantity of onions skin, the quantity of organic sulfur, and the quantity of fenugreek seeds in a fourth quantity of water to form a second final mixture. In other words, all the ingredients are boiled together to form the second final mixture. Subsequently, the method may be continued by straining the second final mixture with a cheesecloth and strainer to form the detangler solution. Further, the detangler solution may be transferred to spray bottles for application. In this embodiment, preferably, the fourth quantity of water is approximately 4 gallons or enough to cover all the ingredients.

In a second alternate embodiment, the quantity of fenugreek seeds and the quantity of sulfur is transferred into a first mesh bag and added into the potato water solution immediately after removing the quantity of potatoes. This is so that the mesh bag may be easily removed after all the potent beneficial properties have seeped into the potato water.

Figure 6:
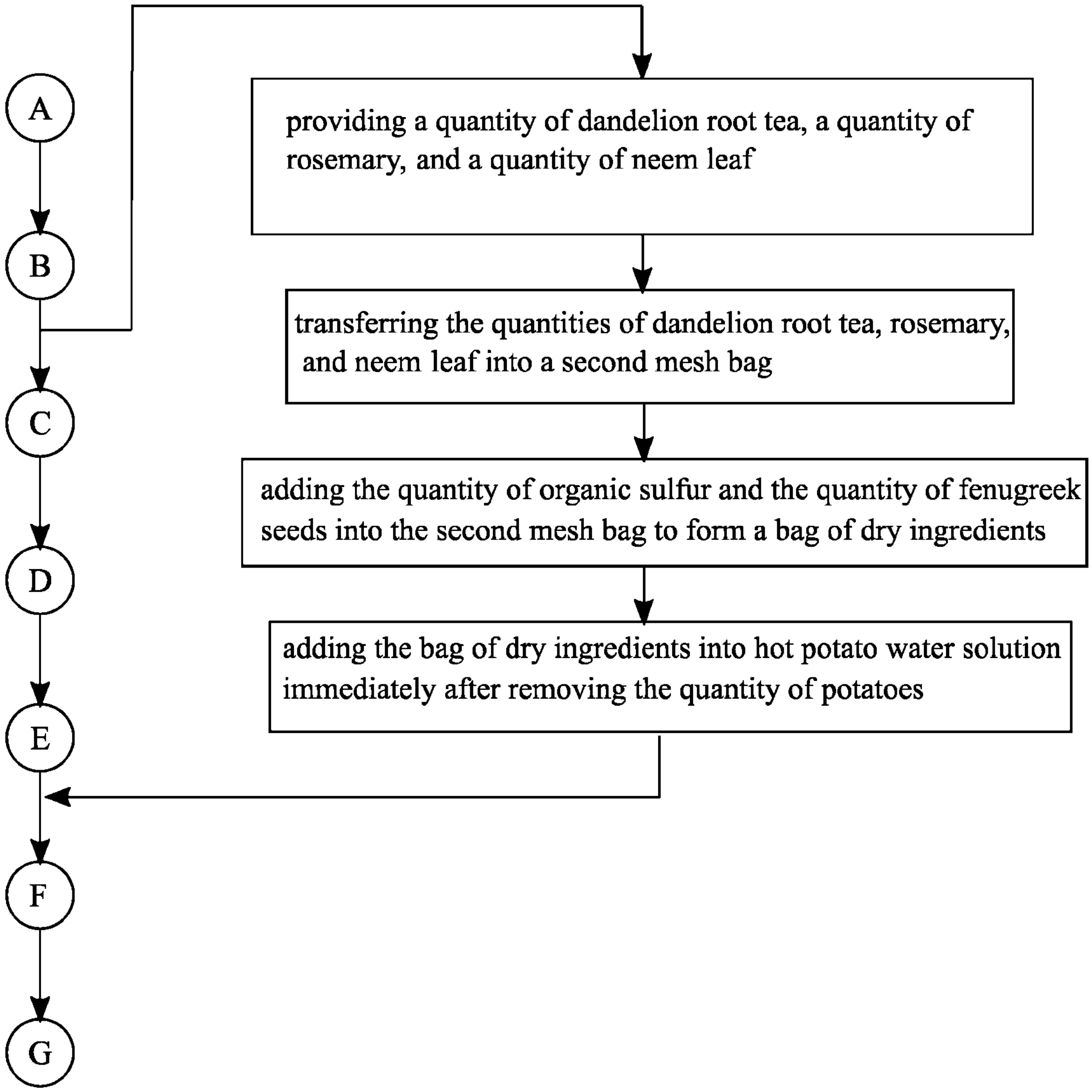
FIG. 6 is a flowchart illustrating a subprocess of the present invention.

In reference to FIG. 6 a subprocess of the present invention is illustrated. In the subprocess, additional ingredients are added to the detangler solution. The sub-process comprises the steps of providing a quantity of dandelion root tea, a quantity of rosemary, and a quantity of neem leaf. Dandelion root is particularly beneficial for hair growth because it contains magnesium, potassium, iron, choline, calcium, phosphorus, and many vitamins. These nutrients feed the scalp and follicles which results in healthy, strong and fast-growing hair. Further, dandelion root is a rich source of vitamins A, C, and E as well as B complex vitamins. Rosemary increases the blood circulation in the scalp keeping the nerve ends healthy. Rosemary also removes excess dirt, and oil, and improves the thickness of hair, and reduces hair fall. Rosemary further contains carnosic acid, which is known to have a healing effect in the case of nerve damage. Furthermore, rosemary can prevent premature greying. Thus, being a combination of antifungal and decongestant properties, rosemary is perfect to help deal with dandruff. Not only does it keep the scalp clear of fungus, which can give way to dandruff, but will also eliminate excess oil. A clean scalp ensures that users stay clear of dandruff and keep their tress healthy. Neem leaves are a great source of fatty acids, vitamins and minerals needed for healthy hair. Some of the benefits of neem leaves for hair include, but are not limited to, treats dandruff and itchy scalp, promotes hair growth, prevents premature greying, and hydrates dry ends. Preferably, each of the quantity of dandelion root tea, the quantity of rosemary, and the quantity of neem leaf is approximately half a cup. The subprocess continues by transferring the quantities of dandelion root tea, rosemary, and neem leaf into a second mesh bag, followed by adding the quantity of organic sulfur and the quantity of fenugreek seeds into the second mesh bag to form a bag of dry ingredients. Thus, all the dry ingredients are placed together in the mesh bag for easy removal. Further, the bag of dry ingredients is added into the hot potato water solution immediately after removing the quantity of potatoes. In other words, the bag of dry ingredients is let to seep in the hot potato water until cool and then the fermented onion water and the fermented rice water are added. Everything is strained with a cheese cloth and transferred into bottles or storage containers.

Figure 7:
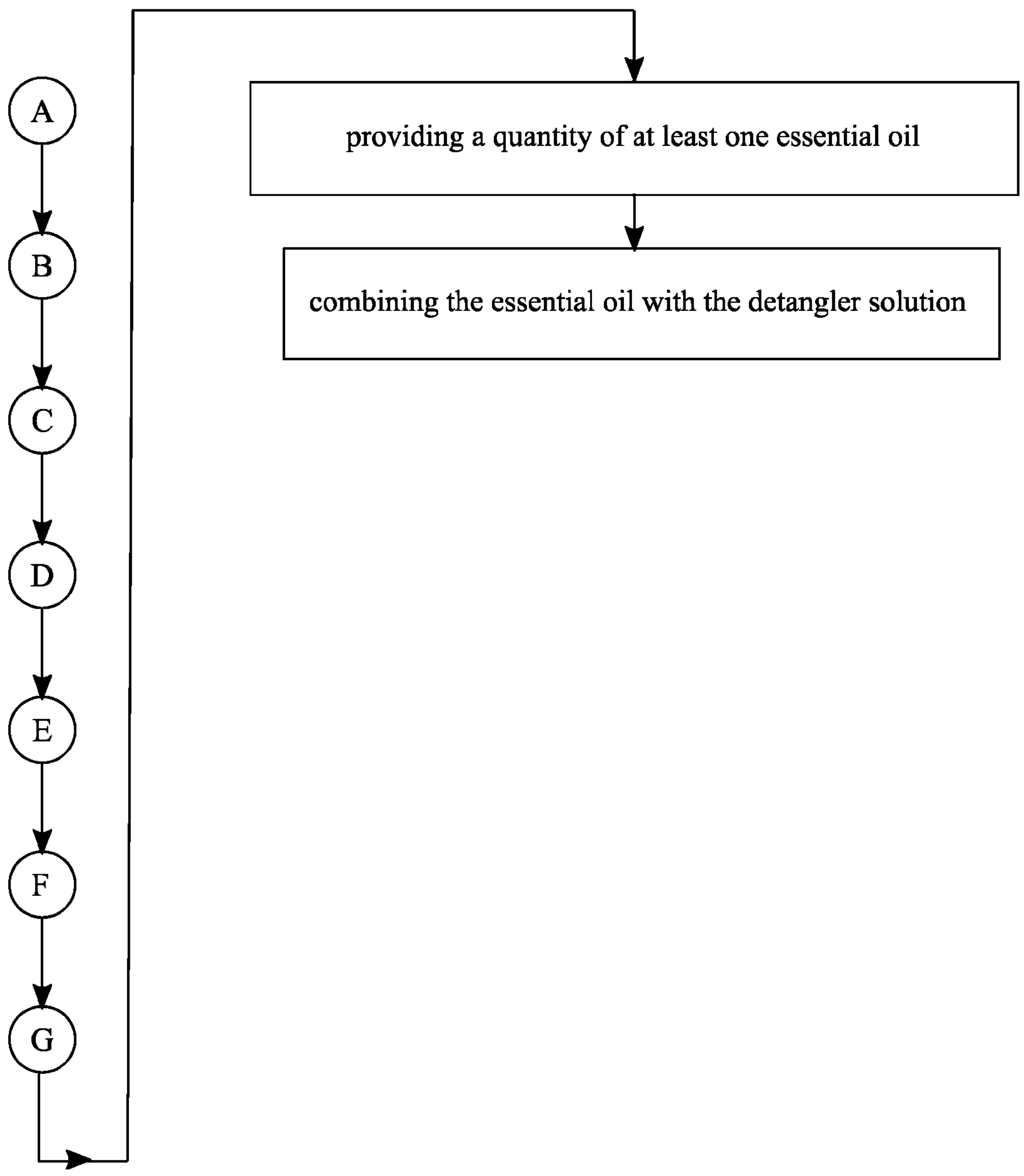
FIG. 7 is a flowchart illustrating a subprocess of the present invention.

In reference to FIG. 7, a sub-process of the overall method comprises the steps of providing a quantity of at least one essential oil and combining the essential oil with the detangler solution. Preferably, the essential oil comprises at least one of lavender oil and rosemary oil. Scenting agents such as essential oils, powders, and other substances of choice, that are known to one of ordinary skill in the art may be added to the detangler solution, as long as the intents of the present invention are not altered. Further, the quantity of essential oil approximately ranges between one drop to 4 ounces of liquid.

Although the invention has been explained in relation to its preferred embodiment, it is to be understood that many other possible modifications and variations can be made without departing from the spirit and scope of the invention as hereinafter claimed.

What is claimed is:

1. A method of manufacturing a hair detangler and conditioner, the method comprising the steps:

(A) providing a first quantity of water, a quantity of potato, a second quantity of water, a quantity of rice, a third quantity of water, a quantity of onions skin, a quantity of organic sulfur, and a quantity of fenugreek seeds;

(B) boiling the quantity of potato in the first quantity of water, and removing the boiled potato, to form a potato water solution;

(C) fermenting the quantity of rice in the second quantity of water for three to seven days, and straining the rice, in order to form a rice water solution;

(D) fermenting the quantity of onion skin in the third quantity of water for three to seven days, and straining the onion skin, to form an onion water solution;

(E) adding the quantity of organic sulfur and the quantity of fenugreek seeds into the potato water solution and allowing to sit for a period of time, to form a slurry solution;

(F) mixing the rice water solution and the onion water solution into the slurry solution to form a first final mixture; and (G) straining the first final mixture with a cheesecloth and strainer to form a detangler solution and transferring the detangler solution into spray bottles for application.

2. The method as claimed in claim 1, wherein the first quantity of water is approximately four gallons of filtered acidic water with a PH (potential of hydrogen) level that is below nine.

3. The method as claimed in claim 1, wherein the quantity of potatoes is approximately five pounds.

4. The method as claimed in claim 1, wherein the second quantity of water is approximately 24 ounces of filtered acidic water with a PH level that is below 9.

5. The method as claimed in claim 1, wherein the quantity of rice is approximately half a cup.

6. The method as claimed in claim 1, wherein the third quantity of water is approximately 24 ounces of filtered acidic water with a PH level that is below 9.

7. The method as claimed in claim 1, wherein the quantity of onion skin is approximately 24 ounces.

8. The method as claimed in claim 1, wherein each of the quantity of fenugreek seeds and the quantity of organic sulfur is two tablespoons.

9. The method as claimed in claim 1, wherein the quantity of fenugreek seeds and the quantity of sulfur is transferred into a first mesh bag and added into the potato water solution immediately after removing the quantity of potatoes.

10. The method as claimed in claim 1, comprising the steps of:

providing a quantity of dandelion root tea, a quantity of rosemary, and a quantity of neem leaf;

transferring the quantities of dandelion root tea, rosemary, and neem leaf into a second mesh bag;

adding the quantity of organic sulfur and the quantity of fenugreek seeds into the second mesh bag to form a bag of dry ingredients; and adding the bag of dry ingredients into the potato water solution immediately after removing the quantity of potatoes.

11. The method as claimed in claim 10, wherein each of the quantity of dandelion root tea, the quantity of rosemary, and the quantity of neem leaf is approximately half a cup.

12. The method as claimed in claim 1, comprising:

providing a quantity of at least one essential oil; and combining the quantity of the at least one essential oil with the detangler solution.

13. The method as claimed in claim 12, wherein the essential oil comprises at least one of lavender oil and rosemary oil.

14. The method as claimed in claim 12, wherein the quantity of the at least one essential oil approximately ranges between one drop to 4 ounces of liquid.

15. A method of manufacturing a hair detangler and conditioner, the method comprising the steps:

(A) providing a first quantity of water, a quantity of potato, a second quantity of water, a quantity of rice, a third quantity of water, a quantity of onions skin, a quantity of organic sulfur, and a quantity of fenugreek seeds;

(B) boiling the quantity of potato in the first quantity of water, and removing the boiled potato, to form a potato water solution;

(C) fermenting the quantity of rice in the second quantity of water for three to seven days, and straining the rice, in order to form a rice water solution;

(D) fermenting the quantity of onion skin in the third quantity of water for three to seven days, and straining the onion skin, to form an onion water solution;

(E) adding the quantity of organic sulfur and the quantity of fenugreek seeds into the potato water solution and allowing to sit for a period of time, to form a slurry solution;

(F) mixing the rice water solution and the onion water solution into the slurry solution to form a first final mixture, wherein the slurry solution has cooled down to room temperature; and (G) straining the first final mixture with a cheesecloth and strainer to form a detangler solution and transferring the detangler solution into spray bottles for application.

16. The method as claimed in claim 15, comprising the steps of:

providing a quantity of dandelion root tea, a quantity of rosemary, and a quantity of neem leaf;

transferring the quantities of dandelion root tea, rosemary, and neem leaf into a second mesh bag;

adding the quantity of organic sulfur and the quantity of fenugreek seeds into the second mesh bag to form a bag of dry ingredients; and adding the bag of dry ingredients into-het the potato water solution immediately after removing the quantity of potatoes.

17. The method as claimed in claim 15, comprising:

providing a quantity of at least one essential oil; and combining the quantity of the at least one essential oil with the detangler solution.

18. The method as claimed in claim 15, wherein each of the first quantity of water, the second quantity of water, and the third quantity of water is filtered acidic water with a PH (potential of hydrogen) level that is below nine.

* * * * *